(12) United States Patent
Kim

(10) Patent No.: US 10,905,891 B2
(45) Date of Patent: Feb. 2, 2021

(54) PORTABLE AUTOMATED EXTERNAL DEFIBRILLATOR

(71) Applicant: Linus Kim, Gyeonggi-do (KR)

(72) Inventor: Linus Kim, Gyeonggi-do (KR)

( * ) Notice: Subject to any disclaimer, the term of this patent is extended or adjusted under 35 U.S.C. 154(b) by 228 days.

(21) Appl. No.: 16/114,536

(22) Filed: Aug. 28, 2018

(65) Prior Publication Data

US 2019/0299015 A1 Oct. 3, 2019

(30) Foreign Application Priority Data

Mar. 28, 2018 (KR) .................. 10-2018-0035550

(51) Int. Cl.
*A61N 1/39* (2006.01)

(52) U.S. Cl.
CPC ......... *A61N 1/3904* (2017.08); *A61N 1/3931* (2013.01); *A61N 1/3975* (2013.01); *A61N 1/3993* (2013.01)

(58) Field of Classification Search
CPC .. A61N 1/3904; A61N 1/3931; A61N 1/3975; A61N 1/3993; A61N 1/3925; A61N 1/046
See application file for complete search history.

(56) References Cited

U.S. PATENT DOCUMENTS

| | | | |
|---|---|---|---|
| 6,327,507 B1* | 12/2001 | Buchan | A61N 1/02 191/12.4 |
| 7,072,712 B2* | 7/2006 | Kroll | A61N 1/39 607/36 |
| 8,615,295 B2* | 12/2013 | Savage | A61N 1/0492 607/5 |
| 9,226,679 B2* | 1/2016 | Balda | A61B 5/0006 |
| 2011/0077497 A1* | 3/2011 | Oster | A61B 5/04087 600/372 |
| 2016/0271408 A1* | 9/2016 | Newton | A61N 1/3904 |

FOREIGN PATENT DOCUMENTS

KR 10-1328866 B1 11/2013

* cited by examiner

*Primary Examiner* — Mark Bockelman
(74) *Attorney, Agent, or Firm* — The PL Law Group, PLLC

(57) ABSTRACT

A portable automated external defibrillator includes a body and an accessory. The body includes a sub power source, a main controller, and a cable winding unit inside the body, an operation button on a front surface of the body, a main electrode pad on a rear surface of the body, and a plug on a side of the body and to which a cable wound on the cable winding unit is coupled. The accessory includes a main power source and a sub-controller inside the accessory, a sub-electrode pad on a rear surface of the accessory, and an outlet on a side of the accessory. The portable automated external defibrillator may prevent a cable of the electrode pad from being twisted or broken, and stably perform an electric shock by the main power source kept in an inactive state during carrying and which is activated in use.

9 Claims, 3 Drawing Sheets

PORTABLE AUTOMATED EXTERNAL DEFIBRILLATOR

CROSS-REFERENCE TO RELATED APPLICATION AND CLAIM OF PRIORITY

This application claims priority to Korean Patent Application No. 10-2018-0035550 filed on Mar. 28, 2018 in the Korean Intellectual Property Office (KIPO), the entire disclosure of which is incorporated by reference herein.

FIELD OF THE INVENTION

The present invention relates to a portable automated external defibrillator, and, more particularly, to a portable automated external defibrillator that is wearable to a wrist or ankle to make it easy to carry and that is used to rescue lives in an emergency situation, in which heartbeats are stopped, by applying an electric shock while being attached to a body of a patient with impaired cardiac function.

DESCRIPTION OF THE RELATED ART

Generally, an automated external defibrillator is a tool bringing a normal heart rhythm by an electric shock for a patient with a cardiac arrest due to ventricular fibrillation or ventricular tachycardia. It is made for people who don't have medical knowledge to easily use it.

Accordingly, a country has a tendency to install the automated external defibrillator in a public place where many people gather, which contributes substantially to improving survival rates in patients with cardiac failure according to various studies.

Particularly, based on Emergency Medical Service Act in Korea, it is mandatory to install the automated external defibrillator in public health facilities, ambulances, passenger aircrafts and airports, railway carriages, ships of more than 20 tons, and multi-use facilities.

The automated external defibrillators provided in the aforementioned public places are relatively bulky, and when an emergency situation occurs, one has to move to the location where the automated external defibrillator is installed, and then, transport it back to the location where the emergency patient is located, which results in substantially delay in the prompt treatment.

In particular, for the cases when the automated external defibrillator should be used, ventricular fibrillation or ventricular tachycardia develops to the cardiac arrest in 4 minutes, and the delayed first aid causes cerebral infarction or vascular disease.

To solve this problem, Korean Patent No. 1,328,866 discloses a portable device with an automatic defibrillation function, the device including: a body with an automatic defibrillation function; and an earphone connected to the body and outputting an electric shock necessary for defibrillation, where the earphone further includes a connection unit connected to the body, a head connected to the connection and outputting the electric shock to the outside, an adhesive member attached to the head, and a cover coupled to the head to cover the adhesive member. However, the earphone type has a problem in which a cable may be easily broken down due to the twist thereof upon carrying.

Moreover, various devices, e.g., a mobile phone, notebook, PMP, MP3, etc. may be used for a body supplying electricity to an electrode of the automated external defibrillator which consumes a relatively large power. However, the devices are used continuously in a daily life, and therefore, when an emergency situation actually requiring the automated external defibrillator occurs, it is problematic they are unable to supply enough power.

SUMMARY

The present invention is conceived to solve one or more of the foregoing problems, and provides a portable automated external defibrillator capable of preventing an electrode cable from being twisted or damaged during carrying.

In addition, an embodiment of the present invention provides a portable automated external defibrillator capable of stably supplying sufficient power to each electrode when a defibrillation function is performed.

Other objects of the present invention will become more apparent through the preferred embodiments described below.

According to an aspect of the present invention, a portable automated external defibrillator includes a body and an accessory, wherein the body includes a sub power source, a main controller, and a cable winding unit provided inside the body, an operation button provided on a front surface of the body, a main electrode pad provided on a rear surface of the body, and a plug provided on a side of the body and to which a cable wound on the cable winding unit is coupled, wherein the accessory includes a main power source and a sub-controller provided inside the accessory, a sub-electrode pad provided on a rear surface of the accessory, and an outlet provided on a side of the accessory and from which the power source plug is detached.

According to other aspect of the present invention, the main power source and the sub-controller operate when the plug is coupled to the outlet, and power is supplied to the main electrode pad and the sub-electrode pad by the operation button, and the body and the accessory each further include a band.

According to another aspect of the present invention, the main electrode pad and the sub-electrode pad are each covered with a detachable protective film or a protective cover, and at least one of a voice guidance unit, a communication unit, and a human body signal detection sensor is further included in the body or the accessory, and the main power source is a graphene storage battery.

The portable automated external defibrillator according to the present invention may prevent a cable of the electrode pad from being twisted or broken during carrying. Further, the portable automated external defibrillator according to the present invention may stably perform an electric shock which consumes a relatively large power, by the main power source which is kept in an inactive state during carrying and which is activated in use.

In addition, the portable automated external defibrillator according to the present invention may be always worn on a user's wrist or ankle by the band, and the portability thereof is improved by adding a waterproof function.

DETAILED DESCRIPTION

Figure 1:
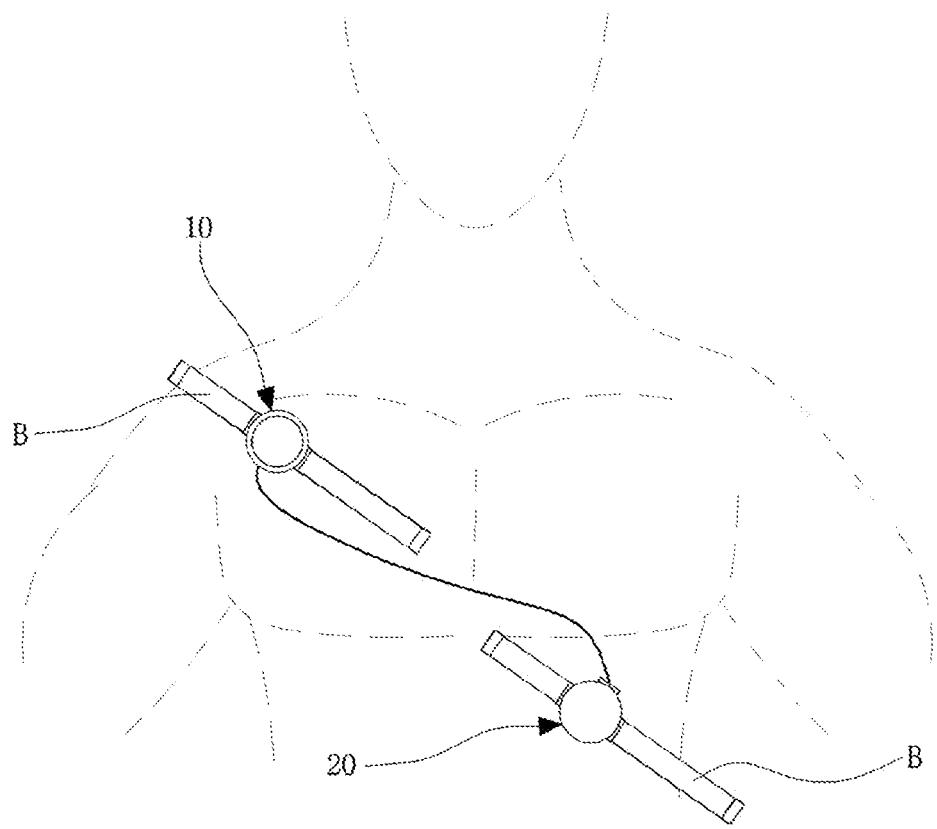
FIG. 1 is an exemplary use view of a portable automated external defibrillator in accordance with an embodiment of the present invention.

The present invention may be applied with various modifications and may have various embodiments. Accordingly, the present invention is intended to be illustrated by specific embodiments in the drawings and described in detail in the detailed description. However, it should be understood that the present invention is not intended to be limited to particular embodiments, but includes all modifications, equivalents, and alternatives falling within the spirit and scope of the present invention. In the following description, when it is considered that the detailed description of the related known art may blur the gist of the present invention, the detailed description thereof will be omitted.

The terms first, second, etc. may be used to describe various elements, but the elements should not be limited by the terms. The terms are used only for the purpose of distinguishing one component from another.

The term used herein is only used to describe the particular embodiments, and is not intended to limit the present invention. Unless the context clearly means otherwise, the singular expression includes plural expression. It should be understood that, herein, the terms "comprises" or "have," etc. are intended to specify that there is a stated feature, number, step, operation, component, part, or a combination thereof herein, and it does not exclude in advance the possibility of presence or addition of one or more other features, numbers, steps, operations, components, parts, or combinations thereof. Hereinafter, embodiments of the present invention will be described in detail with reference to the accompanying drawings.

Figure 2A:
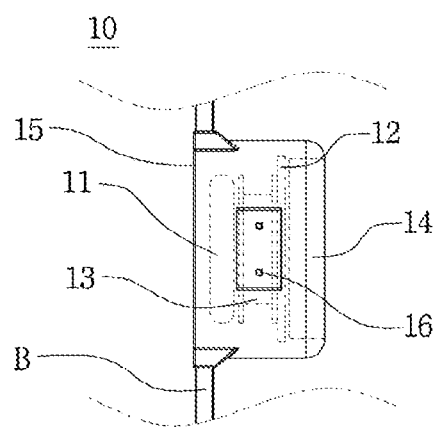
FIGS. 2A and 2B are each a side view of a body and a side view of an accessory of a portable automated external defibrillator in accordance with an embodiment of the present invention.
Figure 2B:
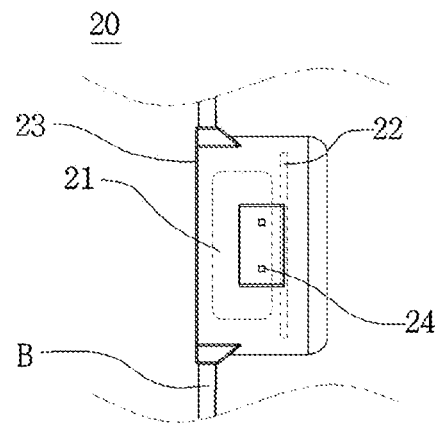

FIG. 1 is an exemplary use view of a portable automated external defibrillator in accordance with an embodiment of the present invention, and FIGS. 2A and 2B respectively are side views of a body and an accessory of a portable automated external defibrillator in accordance with an embodiment of the present invention.

Figure 3A:
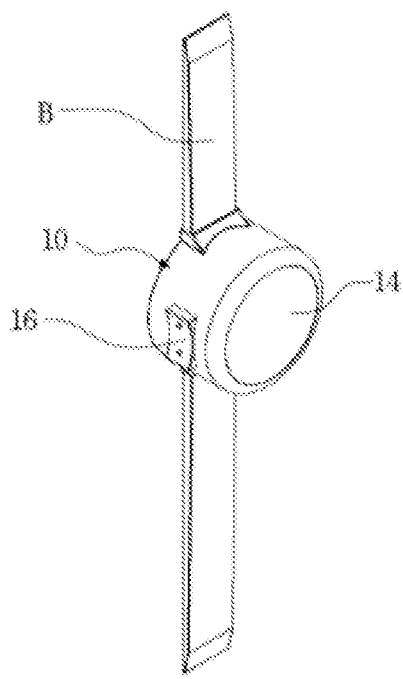
FIGS. 3A and 3B are each a perspective view of a body and a perspective view of an accessory of a portable automated external defibrillator in accordance with an embodiment of the present invention.
Figure 3B:
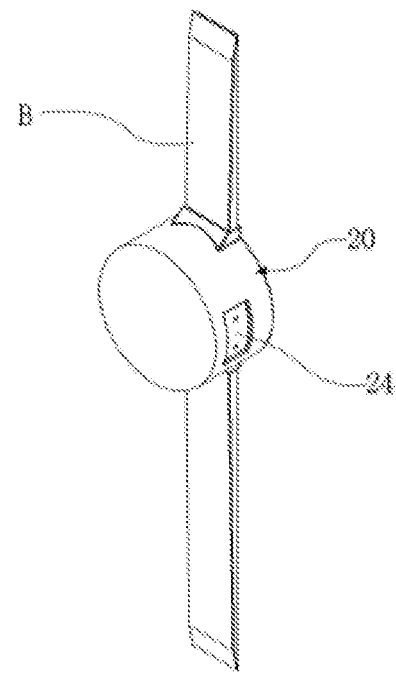
Figure 4A:
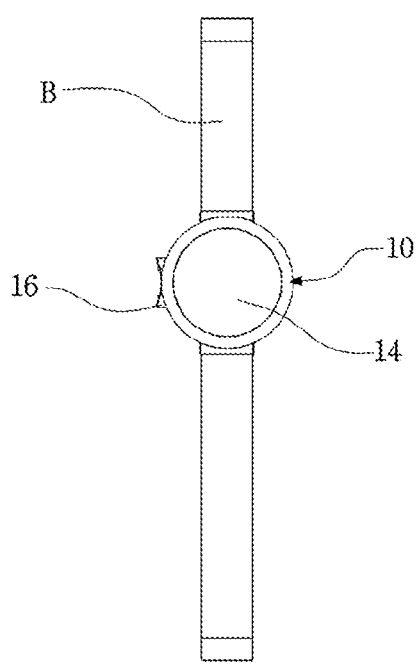
FIGS. 4A and 4B are each a front view of a body and a front view of an accessory of a portable automated external defibrillator in accordance with an embodiment of the present invention.
Figure 4B:
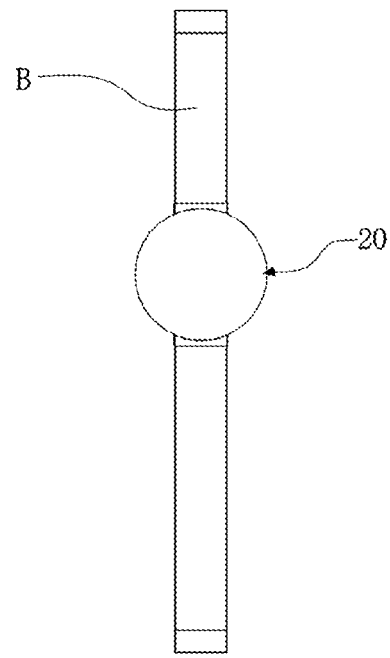

FIGS. 3A and 3B respectively are perspective views of a body and an accessory of a portable automated external defibrillator in accordance with an embodiment of the present invention, and FIGS. 4A and 4B respectively are front views of a body and an accessory of a portable automated external defibrillator in accordance with an embodiment of the present invention. Referring to these, the constitution of the present invention is explained as follows.

A portable automated external defibrillator includes a body 10 and an accessory 20, wherein the body 10 includes a sub power sourcell, a main controller 12, and a cable winding unit 13 provided inside the body, an operation button 14 provided on a front surface of the body, a main electrode pad 15 provided on a rear surface of the body, and a plug 16 provided on a side of the body and to which a cable wound on the cable winding unit 13 is coupled, wherein the accessory 20 includes a main power source 21 and a sub-controller 22 provided inside the accessory, a sub-electrode pad 23 provided on a rear surface of the accessory, and an outlet 24 provided on a side of the accessory and from which the power source plug is detached.

The main electrode pad 15 and the sub-electrode pad 23 are covered with a conductive adhesive so as to be attached to a human body, and each of them is covered with a detachable protective film or a protective cover which is to be removed in use. Here, the main electrode pad 15 and the sub-electrode pad 23 are divided to describe the characteristics of the portable automated external defibrillator according to the separation of the body 10 and the accessory 20, and are means for performing the same structure and function.

The operation button 14 is preferably configured to be depressed without protruding to a front surface of the body 10 in order to prevent the operation button 14 from being pressed by an external force applied during carrying. An electronic timepiece for confirming the time may be included in a front surface of the operation button 14.

The plug 16 may be further provided with a nail groove or protrusion on one side to facilitate separation from the body 10.

The cable winding unit 13 may be configured to hold and fix the cable while the cable is pulled so that the plug 16 is not separated and rattled from the body 10 by an elastic member such as a leaf spring or the like. Also, the cable winding unit 13 may be configured to prevent the cable from being wound by releasing or fixing the elastic force when the cable is released over a certain length to be coupled to the accessory 20 in use.

The detailed configuration of the foregoing cable winding unit 13 is omitted because a variety of cable winding device technologies such as a charging cable winding device, an ear-set cable winding device, or the like are known.

As described above, by winding the cable connecting the main electrode pad 15 and the sub-electrode pad 23 on the cable winding unit 13 and keeping the cable inside the body 10 during carrying, it is possible to obstruct breaking or defective connection due to cable twisting or the like occurring during carrying, thereby preventing the portable automated external defibrillator from malfunctioning in the emergency.

When the plug 16 is coupled to the outlet 24, the main power source 21 and the sub-controller 22 operate, and power is supplied to the main electrode pad 15 and the sub-electrode pad 23 by the operation button 14.

In other words, the accessory 20 is in an off state without any special function during carrying, and operates when it is coupled to the body 10 by the plug 16 for use. This is for supplying sufficient power to the main electrode pad 15 and the sub-electrode pad 23 each in use by eliminating or minimizing the power consumption of the main power source 21 during carrying.

Accordingly, even when the operation button 14 is pressed by the external force during carrying, no particular operation is performed, thereby allowing to prevent the risk of electric shock or the like.

At least one of a voice guidance unit, a communication unit, and a human body signal detection sensor may be further included in the body 10 or the accessory 20 to add a feature such a smart band.

However, it is preferable that when it is provided inside the accessory 20, it is activated when being coupled to the body 10 by the plug 16, whereas the sub power source 11 provided inside the body 10 may be provided inside the body 10 to sustain power consumption during carrying.

The main power source 21 of the accessory 20 supplies sufficient power to the main electrode pad 15 and the sub-electrode pad 23 each in use. The main power source 21 of the accessory 20 has a high performance and is bulky compared to the sub power source 11. Therefore, components in the inside of the accessory 20 should be minimized to ensure sufficient space. Particularly, the main power source 21 is preferably applied with a graphene storage battery, and may be applied with a storage battery of a flat layered type applying to an implantable cardiac defibrillator.

The body 10 and the accessory 20 each may further include a band B. The band B may be made of leathers, metals, or synthetic resin materials with elastic quality, as the same as or similar to a watchstrap, for easy carrying. Further, the structure and material of various known detachable bands may be applied to the band B so that the band B can be easily detached from the wrist, ankle, or the like.

The body 10 and the accessory 20 may be coupled in a single band B and carried. Also, a fastening structure such as a hook, a fastening groove, or the like may be further provided on an each outside of the body 10 and the accessory 20 so as to be carried in a coupled state between the body 10 and the accessory 20.

In addition, both the body 10 and the accessory 20 may further include a waterproof function to improve the portability. The body 10 and the accessory 20 each further include a charging terminal.

Figure 5A:
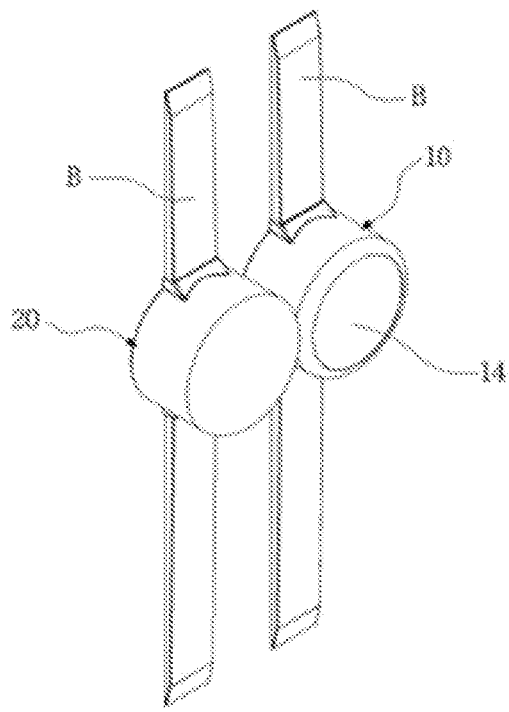
FIGS. 5A and 5B are a perspective view and a front view, respectively, of a combination of a body and an accessory of a portable automated external defibrillator in accordance with an embodiment of the present invention.
Figure 5B:
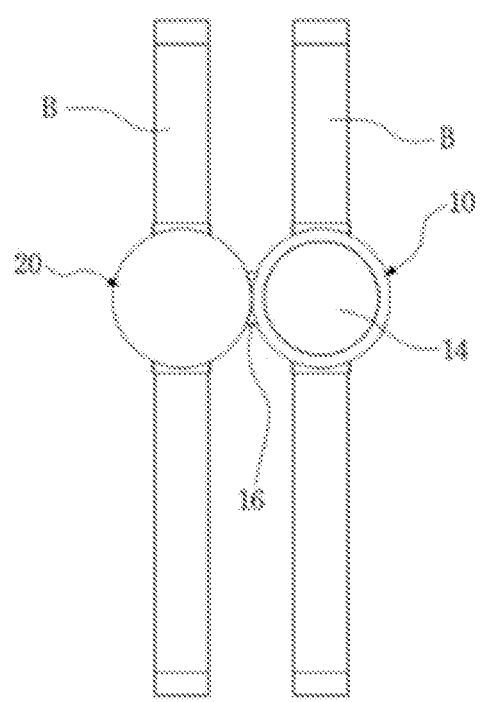

FIGS. 5A and 5B are a perspective view and a front view of a combination of a body and an accessory of a portable automated external defibrillator in accordance with an embodiment of the present invention, respectively, and in particular, are combined state views in which the cable is not extended. Referring to these, the portable automated external defibrillator as described above is used as follows.

If there is a patient with ventricular fibrillation or ventricular tachycardia, a protective film or a protective cover is removed, and the main electrode pad 15 and the sub-electrode pad 23 are each attached to a body of the patient. In other words, the main electrode pad 15 and the sub-electrode pad 23 are each provided on a lower surface of the body 10 and the accessory 20 so that the body 10 and the accessory 20 themselves are attached to the body of the patient by a conductive adhesive.

Here, more preferably, the body 10 is attached to a lower side of a right collarbone of the patient, and the accessory (20) is attached to a midline of an axilla outside a left nipple of the patient.

After that, one pulls the plug 16 to unfold and extend the cable wound on the cable winding unit 13 and couples it to the outlet 24. Conversely, the plug 16 and the outlet 24 may be coupled and then attached to the body of the patient.

Here, the main power source 21 and the sub-controller 22 are activated by being signaled that the plug 16 and the outlet 24 are coupled.

The cable may be a power cable for supplying power only. However, preferably, the cable may be a cable for transmitting a signal so that the sub-controller 22 may receive a control signal of the main controller 12.

An electrocardiogram sensor provided inside the body 10 detects a heartbeat of the patient while attached to the body of the patient, and accordingly, the main controller 12 calculates an appropriate amount of electric shock. Then, when the operation button 14 is pressed, electric shock is applied to the body of the patient through the main electrode pad 15 and the sub-electrode pad 23.

Here, a voice guidance unit may be provided inside the body 10 or the accessory 20 to notify the user whether the operation button 14 is to be pushed according to the detected heartbeat.

If the user presses the operation button 14, there is a risk of electric shock. Therefore, it is preferable that the body 10 and the accessory 20 each except for the main electrode pad 15 and the sub-electrode pad 23 and the band B, are made of an insulator.

A communication unit and a GPS sensor may be further provided inside the body 10 or the accessory 20 to send an emergency relief signal when the main power source 21 and the sub-controller 22 are activated by being signaled that the plug 16 and the outlet 24 are coupled.

The foregoing preferred embodiments of the present invention have been disclosed for the purpose of illustration, and it would be possible for those skilled in the art to make various modifications, alterations, and additions thereof within the spirit and scope of the invention. Further, it would be appreciated that such modifications, alterations, and additions fall within the scope of the following claims.

What is claimed is:

1. A portable automated external defibrillator, comprising:
   a body comprising:
      a sub power source provided inside the body;
      a main controller provided inside the body;
      a cable winding unit provided inside the body;
      an operation button provided on a front surface of the body;
      a main electrode pad provided on a rear surface of the body; and
      a plug provided on a side of the body; and
      a cable wound on the cable winding unit, the cable is coupled to the plug; and
   an accessory comprising:
      a main power source provided inside the accessory;
      a sub-controller provided inside the accessory;
      a sub-electrode pad provided on a rear surface of the accessory; and
      an outlet provided on a side of the accessory and from which the power source plug is detached,
      wherein the accessory is in an off state during carrying, and operates only when it is coupled to the body; and
      only when the plug is coupled to the outlet, the main power source and the sub-controller operate, and power is supplied to the main electrode pad and the sub-electrode pad by the operation button.

2. The portable automated external defibrillator of claim 1, wherein the body and the accessory each comprise a band.

3. The portable automated external defibrillator of claim 1, wherein the main electrode pad and the sub-electrode pad are each covered with a detachable protective film or a protective cover.

4. The portable automated external defibrillator of claim 1, wherein at least one of a voice guidance unit, a communication unit, and a human body signal detection sensor is further provided in the body or the accessory.

5. The portable automated external defibrillator of claim 1, wherein the main power source is a graphene storage battery.

6. The portable automated external defibrillator of claim 1, wherein the body and the accessory each comprise a band.

7. The portable automated external defibrillator of claim 1, wherein the main electrode pad and the sub-electrode pad are each covered with a detachable protective film or a protective cover.

8. The portable automated external defibrillator of claim 1, wherein at least one of a voice guidance unit, a communication unit, and a human body signal detection sensor is further provided in the body or the accessory.

9. The portable automated external defibrillator of claim 1, wherein the main power source is a graphene storage battery.

\* \* \* \* \*